(12) United States Patent
Kim et al.

(10) Patent No.: US 6,797,739 B1
(45) Date of Patent: Sep. 28, 2004

(54) TRIAZENE-BASED COMPOUND COMPRISING FUNCTIONALIZED ALKYLTHIO GROUPS, AND PHOTOPOLYMERIZATION INITIATOR

(75) Inventors: Sung-Hyun Kim, Taejeon (KR); Chul-Woo Lee, Taejeon (KR); Jin-Seuk Kim, Taejeon (KR); Jae-Hwan Lee, Taejeon (KR); Dong-Chang Choi, Taejeon (KR); Hyuk-Jin Cha, Taejeon (KR)

(73) Assignee: LG Chemical Co., Ltd., Seoul (KR)

( * ) Notice: Subject to any disclaimer, the term of this patent is extended or adjusted under 35 U.S.C. 154(b) by 172 days.

(21) Appl. No.: 10/204,248
(22) PCT Filed: Jun. 12, 2000
(86) PCT No.: PCT/KR00/00619
§ 371 (c)(1), (2), (4) Date: Sep. 27, 2002
(87) PCT Pub. No.: WO01/96317
PCT Pub. Date: Dec. 20, 2001
(51) Int. Cl.[7] .......................... C08F 2/42; C07D 253/00
(52) U.S. Cl. ................. 522/63; 522/8; 522/9; 522/16; 522/26; 522/63; 544/180; 544/193
(58) Field of Search ............................ 522/16, 8, 9, 26, 522/63; 544/180, 193

(56) References Cited

U.S. PATENT DOCUMENTS

| | | | | | |
|---|---|---|---|---|---|
| 4,189,323 A | * | 2/1980 | Buhr | ........................ | 430/281.1 |
| 4,239,850 A | * | 12/1980 | Kita et al. | ................ | 430/281.1 |
| 4,837,128 A | * | 6/1989 | Kawamma et al. | ...... | 430/281.1 |
| 5,116,977 A | * | 5/1992 | Rossman et al. | ........... | 544/113 |
| 5,153,323 A | * | 10/1992 | Rossman et al. | ........... | 544/194 |
| 5,298,361 A | * | 3/1994 | Bonham | ..................... | 430/260 |
| 5,340,697 A | * | 8/1994 | Yoshimoto et al. | ...... | 430/270.1 |
| 5,484,919 A | * | 1/1996 | Bonham | ................... | 544/193.1 |
| 5,723,513 A | * | 3/1998 | Bonham et al. | .............. | 522/63 |
| 5,837,586 A | * | 11/1998 | Perron | ..................... | 430/285.1 |
| 5,847,133 A | * | 12/1998 | Bonham | ..................... | 544/216 |

FOREIGN PATENT DOCUMENTS

| EP | 0 271 195 A1 | 6/1988 |
|---|---|---|
| EP | 0 319 296 A2 | 6/1989 |
| EP | 0 389 236 A2 | 9/1990 |

\* cited by examiner

Primary Examiner—James J. Seidleck
Assistant Examiner—Sanza L. McClendon
(74) Attorney, Agent, or Firm—Birch, Stewart, Kolasch & Birch, LLP (57) ABSTRACT

The preset invention relates to a photosensitive composition, and provides a triazine-based compound comprising new functionalized alkylthio groups of which long term storage characteristics at room temperature as well as photochemical activity as a photopolymerization initiator are superior.

12 Claims, 3 Drawing Sheets

TRIAZENE-BASED COMPOUND COMPRISING FUNCTIONALIZED ALKYLTHIO GROUPS, AND PHOTOPOLYMERIZATION INITIATOR

CROSS REFERENCE TO RELATED APPLICATION

This application is the national phase under 35 U.S.C. § 371 of PCT International Application No. PCT/KR00/00619 which has an International filing date of Jun. 12, 2000, which designated the United States of America.

This application is based on application No. 10-1999-0005368 filed in the Korean Industrial Property Office on Feb. 18, 1999, the contents of which are incorporated hereinto by reference.

BACKGROUND OF THE INVENTION (a) Field of the Invention

The present invention relates to a photosensitive composition, more particularly to a triazine-based compound comprising functionalized alkylthio groups of which long-term storage characteristics at room temperature as well as effects as a photopolymerization initiator are superior when it is used as a photosensitive composition.

(b) Description of the Related Art

Photosensitive compositions are polymerizable compounds having ethylenically unsaturated bonds containing photopolymerization initiators, and are being used in photocurable inks, photosensitive printing plates, varieties of photoresists and color filters for Liquid Crystal Displays, etc., since photosensitive compositions can be polymerized and cured by irradiating light on them.

Although various types of photopolymerization initiators used in these photosensitive compositions include acetophenone derivatives, benzophenone derivatives, acrylphosphine oxide derivatives, triazine derivatives, etc., halomethyl triazine compounds which are decomposed by right irradiation thus generating halogen radicals are frequently among them. Particularly, the sensitivities of 2-aryl-4,6-bis (trihalomethyl)-s-triazine among halomethyl trazine compounds are known to be relatively superior.

For example, the use of a compound using two ringed or multi-ringed aromatic groups, or complex ring type aromatic groups such as No. 2 position aryl group is disclosed, and particularly it is written in Japanese Laid-open Patent Publication No. Showa 53-133428 that good results are obtained by using a naphthyl group as an aryl group. However, the sensitivities of compounds disclosed in Japanese Laid-open Patent Publication No. Showa 53-133428 are not to a degree of satisfaction in the practical applications, and the composition has demerits in that stabilities according to the time lapse of a photosensitive composition are lowered due to its use in large quantities or with a long light irradiation time, as well as insufficient solubility into a polymerizable compound having ethylenically unsaturated bonds.

Furthermore, although it is disclosed in Japanese Laid-open Patent Publication No. Showa 63-70243 that stabilities according to the time lapse of a photosensitive composition can be improved by employing substituents having amide bonds or ester bonds at No. 2 position naphthyl groups in the composition, the sensitivity as a photoinitiator was not satisfactory in that case as well. Additionally, a photoinitiator having less molecular weight and large crystallinity has a problem in that it migrates onto the coated film surface or crystallizes in the film after coatings decreasing the photoinitiation efficiencies.

Methods used to solve these problems include using initiators having strong interactions with binders, photoinitiators with large molecular weights, and multi-functional or poly-functional triazine-based photoinitiators.

A photoinitiator having two or more photoactive triazine groups is disclosed in U.S. Pat. No. 5,298,361 wherein triazine groups are coupled with aliphatic ether, urethane, ester, and amide bonds. 2-Aryl-4,6,-bis(trihalomethyl)-s-triazine based derivatives in which an amino group substituted phenyl group is employed at the No. 2 position are disclosed in U.S. Pat. No. 4,837,128. However, these compounds have limits in the applications requiring color purity since they have maximum absorbance over 350 nm and absorb light within the scope of visible rays despite their superior photoactivities.

Furthermore, 2-aryl-4,6-bis(trihalomethyl)-s-triazine based s derivatives in which phenyl groups coupled with simple alkyl or aryl groups by S, Se, or Te are employed at the No. 2 position are disclosed in European Patent No. 271195 A1. However, these compounds have problems in compatibility with binder polymers used in a photopolymerization composition, and with sublimation in the high temperature process when alkyl groups having less numbers of carbons are substituted, and they have limits in photoiniteation efficiencies with various light sources.

SUMMARY OF THE INVENTION

It is an object of the present invention to provide a triazine-based photoinitiator having functionalized alkylthio groups showing strong absorbance at 360 nm in order to solve existing photoinitiator problems such as compatibility, photoinitiation efficiency, and development process problems.

It is another object of the present invention to provide a compound of which long term storage characteristics at room temperature and effects as a photopolymerization initiator as well as coating characteristics are superior, and in which the development time can be controlled when it is used as a photosensitive composition.

The present invention provides a triazine compound having a functionalized alkylthio group represented in the following Chemical Formula 1, and a photopolymerization initiator comprising an active ingredient of the compound in order to accomplish the above objects.

[Chemical Formula 1]

wherein $R_1$ is selected from the group consisting of $C_nH_{2n}CONH_2$ (n is an integer from 1 to 12), $C_nH_{2n}COOC_mH_{2m+1}$ (n is an integer from 1 to 12 and m is an integer from 0 to 12), $(CH_2)_nCOOC_mH_{2m}OC_lH_{2l+1}$ (n, m, and l are each independent integers from 1 to 12), $(CH_2)_n$COO-cyclo-$C_mH_{2m+1}$ (n is an integer from 1 to 12, and m is an integer from 3 to 12), $C_nH_{2n}COOR_f$ (n is an integer from 1 to 12, and $R_f$ is an alkyl group of which all or some of the hydrogen atoms are substituted with fluorine), and $C_nH_{2n}COOR_6$ (n is an integer from 1 to 12, and $R_6$ is an aryl group having from 6 to 14 carbon atoms or a $C_1$~$C_6$ alkyl group having a $C_6$~$C_{14}$ aryl group); and $R_2$, $R_3$, $R_4$, and $R_5$ are each independently a hydrogen, a halogen, or an alkyl having from 1 to 6 carbon atoms, or alkoxyl groups having from 1 to 6 carbon atoms.

Halomethyl triazine compounds synthesized in order to accomplish the above objects have superior long term storage characteristics at mom temperature, can control the development time according to the employed functionalized alkylthio groups, and have photobleaching effects so that effects as a photopolymerization initiator do not greatly influence color filter photoresists when they are used in manufacturing color filters for liquid crystal displays.

BRIEF DESCRIPTION OF THE DRAWINGS

A more complete appreciation of the invention, and many of the attendant advantages thereof, will be readily apparent as the same becomes better understood by reference to the following detailed description when considered in conjunction with the accompanying drawings, wherein.

DETAILED DESCRIPTION OF THE PREFERRED EMBODIMENTS

Figure 1:
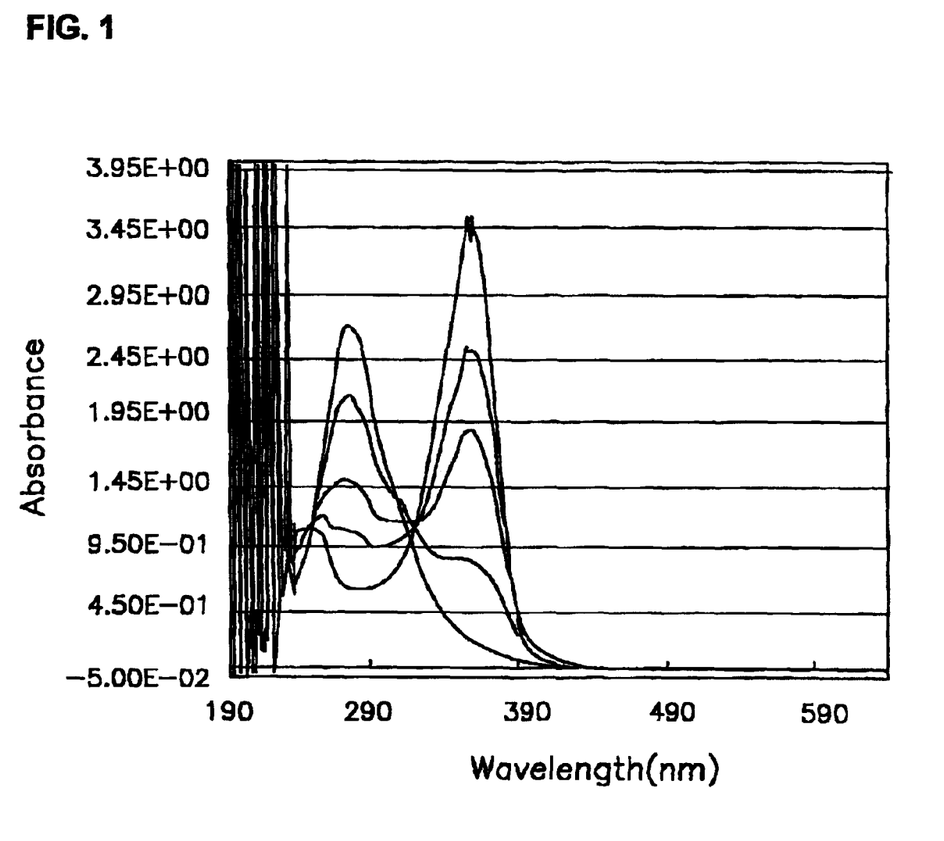
FIG. 1 is an UV-spectrum showing UV-visible absorption characteristics and photobleaching effects of a compound represented as in Chemical Formula 1a prepared in EXAMPLE 1.
Figure 2:
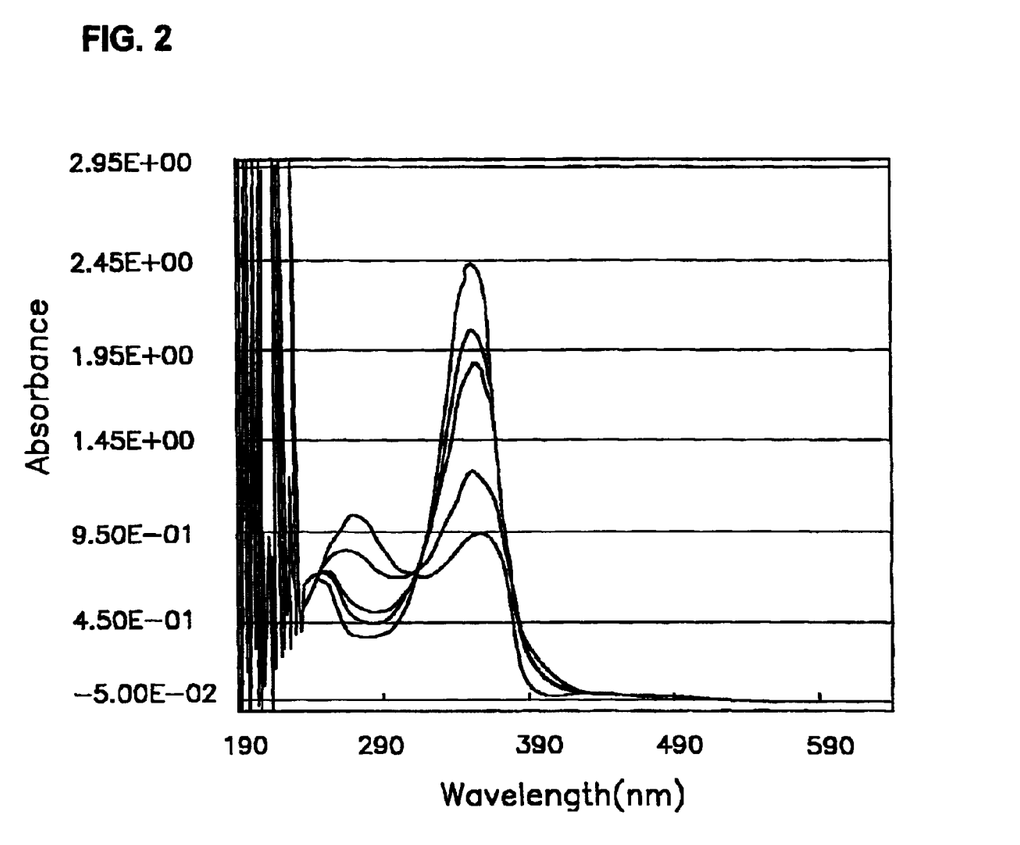
FIG. 2 is an UV-spectrum showing UV-visible absorption characteristics and photobleaching effects of a compound represented as in Chemical Formula 1b prepared in EXAMPLE 2.
Figure 3:
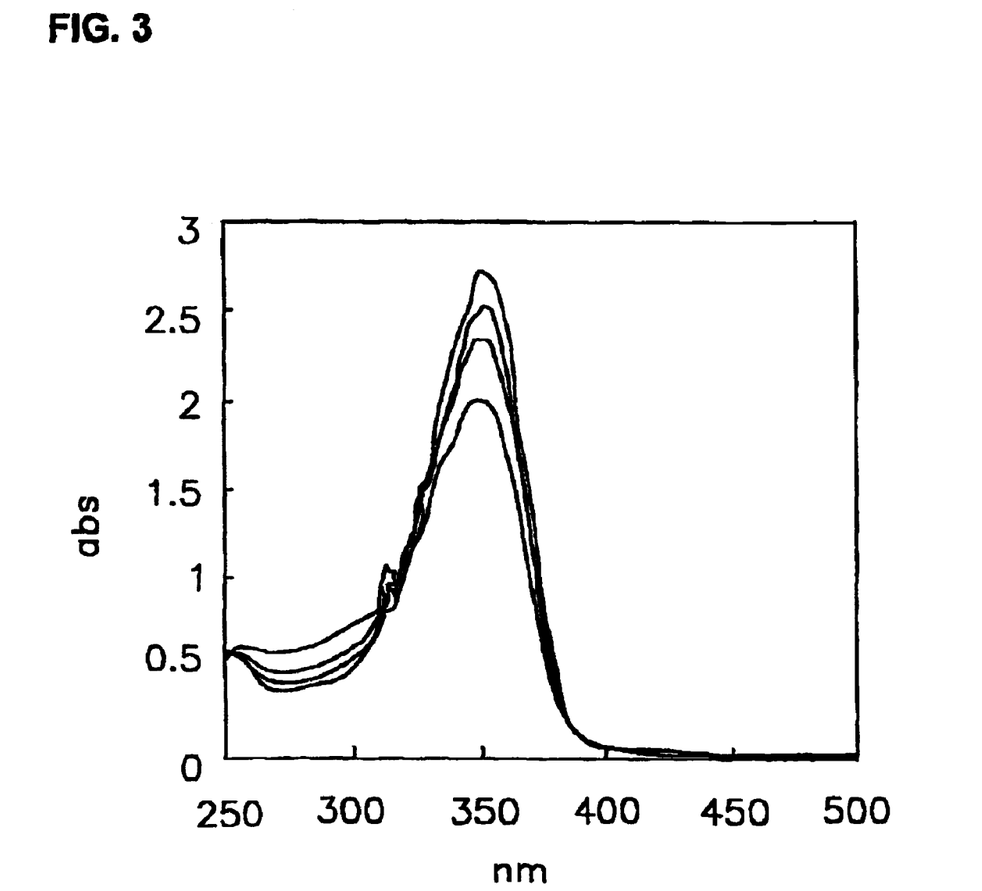
FIG. 3 is an UV-spectrum showing UV-visible absorption characteristics and photobleaching effects of a compound represented as in Chemical Formula 1c prepared in EXAMPLE 3.

In the following detailed description, only the preferred embodiments of the invention have been shown and described, simply by way of illustration of the best mode contemplated by the inventors) of carrying out the invention. As will be realized, the invention is capable of modification in various obvious respects, all without departing from the invention. Accordingly, the description is to be regarded as illustrative in nature, and not restrictive.

The present invention having the above objects is described further in detail as follows:

In a compound represented as in the above Chemical Formula 1, $C_nH_{2n}$, an alkyl group having from 1 to 12 carbon atoms, is selected from the group consisting of methylene, ethylene, 1,2-propylene, 1,3-propylene, 1,4-butylene, pentamethylene, hexamethylene, heptamethylene, octamethylene, nonamethylene, decamethylene, undecamethylene, and dodecamethylene when $R_1$ is $C_nH_{2n}CONH_2$.

$C_nH_{2n}$, an alkyl group having from 1 to 12 carbon atoms, is selected from the group consisting of methylene, ethylene, 1,2-propylene, 1,3-propylene, 1,4-butylene, pentamethylene, hexamethylene, heptamethylene, octamethylene, nonamethylene, decamethylene, undecamethylene, and dodecamethylene; and $C_mH_{2m+1}$, an alkyl group having from 0 to 12 carbon atoms, is selected from the group consisting of hydrogen, methyl, ethyl, propyl, isopropyl, butyl, isobutyl, pentyl, isopentyl, hexyl, heptyl, octyl, 2-ethylhexyl, isooctyl, nonyl, decanyl, undecanyl, and dodecanyl when $R_1$ is $C_nH_{2n}COOC_mH_{2m+1}$.

$(CH_2)_n$, an alkyl group having from 1 to 12 carbon atoms, is selected from the group consisting of methylene, ethylene, 1,2-propylene, 1,3-propylene, 1,4-butylene, pentamethylene, hexamethylene, heptamethylene, octamethylene, nonamethylene, decamethylene, undecamethylene, and dodecamethylene; $C_mH_{2m}$, an alkyl group having from 1 to 12 carbon atoms, is selected from the group consisting of methylene, ethylene, 1,2-propylene, 1,3-propylene, 1,4-butylene, pentamethylene, hexamethylene, heptamethylene, octamethylene, nonamethylene, decamethylene, undecamethylene, and dodecamethylene; and $C_lH_{2l+1}$, an alkyl group having from 1 to 12 carbon atoms, is selected from the group consisting of methyl, ethyl, propyl, isopropyl, butyl, isobutyl, pentyl, isopentyl, hexyl, heptyl, octyl, 2-ethylhexyl, isooctyl, nonyl, decanyl, undecanyl, and dodecanyl when $R_1$ is $(CH_2)_n COOC_mH_{2m}OC_lH_{2l+1}$.

$(CH_2)_n$, an alkyl group having from 1 to 12 carbon atoms, is selected from the group consisting of methylene, ethylene, 1,2-propylene, 1,3-propylene, 1,4-butylene, pentamethylene, hexamethylene, heptamethylene, octamethylene, nonamethylene, decamethylene, undecamethylene, and dodecamethylene, and cyclo-$C_mH_{2m-1}$ is a $C_3$~$C_{12}$ alicyclic group having cyclic groups when $R_1$ is $(CH_2)_n COO$-cyclo-$C_mH_{2m-1}$.

$C_nH_{2n}$, an alkyl group having from 1 to 12 carbon atoms, is selected from the group consisting of methylene, ethylene, 1,2-propylene, 1,3-propylene, 1,4-butylene, pentamethylene, hexamethylene, heptamethylene, octamethylene, nonamethylene, decamethylene, undecamethylene, and dodecamethylene, and $R_1$ is a $C_1$~$C_6$ alkyl group of which all or some of the hydrogen atoms are substituted with fluorine when $R_1$ is $C_nH_{2n}COOR_f$.

$C_nH_{2n}$, an alkyl group having from 1 to 12 carbon atoms, is selected from the group consisting of methylene, ethylene, 1,2-propylene, 1,3-propylene, 1,4-butylene, pentamethylene, hexamethylene, heptamethylene, octamethylene, nonamethylene, decamethylene, undecamethylene, and dodecamethylene, and $R_6$ is an aryl group having from 6 to 14 carbon atoms or a $C_1$~$C_6$ alkyl group having a $C_6$~$C_{14}$ aryl group when $R_1$ is $C_nH_{2n}COOR_6$.

$R_2$, $R_3$, $R_4$, and $R_5$ are each independent hydrogens, halogens, alkyls having from 1 to 6 carbon atoms, or alkoxy groups having from 1 to 6 carbon atoms.

A method for preparing a compound represented as in Chemical Formula 1 of the present invention comprising the steps of synthesizing cyano compounds and preparing a triazine compound having trichloromethyl groups by reacting an alkylthiobenzonitrile compound comprising a functional group represented as in the following Chemical Formula 2 with trichloroacetonitrile ($CCl_3CN$) under the existence of aluminum halide ($AlCl_3$, $AlBr_3$).

[Chemical Formula 2]

wherein $R_1$ is selected from the group consisting of $C_nH_{2n}CONH_2$ (n is an integer from 1 to 12), $C_nH_{2n}COOC_mH_{2m+1}$ (n is an integer from 1 to 12 and m is an integer from 0 to 12), $(CH_2)_n COOC_mH_{2m}OC_lH_{2l+1}$ (n, m, and l are each independent integers from 1 to 12), $(CH_2)_n COO$-cyclo-$C_mH_{2m+1}$ (n is an integer from a to 12, and m is an integer from 3 to 12), $C_nH_{2n}COOR_f$ (n is an integer from 1 to 12, and $R_f$ is an alkyl group of which all or some of the hydrogen atoms are substituted with fluorine), and $C_nH_{2n}COOR_6$ (n is an integer from 1 to 12, and $R_6$ is an aryl group having from 6 to 14 carbon atoms or a $C_1$~$C_6$ alkyl group having a $C_6$~$C_{14}$ aryl group); and $R_2$, $R_3$, $R_4$, and $R_5$ are each independent hydrogens, halogens, alkyls having from 1 to 6 carbon atoms, or alkoxyl groups having from 1 to 6 carbon atoms.

A compound of the present invention is a useful photopolymerization initiator of a polymerizable compound having ethylenically unsaturat d bonds as described in the above, and these polymerizable compounds having ethylenically unsaturated bonds can be used as in the existing photosensitive compositions.

Examples of polymerizable compounds having the above ethylenically unsaturated bonds include: compounds obtained by esterifying α,β-unsaturated carboxylic acid with polyhydric alcohols such as ethylene glycol di(meth) acrylate, polyethylene glycol di(meth)acrylate having from 2 to 14 ethylene groups, trimethylolpropane di(meth) acrylate, trimethylolpropane tri(meth)acrytate, pentaerythritol tri(meth)acrylate, pentaerythritol tetra(meth)acrylate, propylene glycol di(meth)acrylate having from 2 to 14 propylene groups, dipentaerythritol penta(meth) acrylate, dipentaerythritol hexa(meth)acrylate, etc.; compounds obtained by adding (meth)acrylic acid to compounds containing glycidyl groups such as trimethylolpropane triglycidylether, bisphenol A diglycidylether, etc.; adducts obtained by esterifying the compounds having hydroxyl groups and ethylenically unsaturated bonds with phthalic acid, for example, phthalic diester of β-hydroxyethyl (meth) acrylate; toluene diisocyanate adducts of the compounds having hydroxyl groups and ethylenically unsaturated bonds such as β-hydroxyethyl (meth)acrylate, etc.; ester compounds obtained by the reaction of the compounds having hydroxyl groups and ethylenically unsaturated bonds with polyfunctional carboxylic acids; polyisocyanate adducts of the compounds having hydroxyl groups and ethylenically unsaturated bonds; epoxy acrylates obtained by reacting an epoxy resin and (meth)acrylic acids; and alkylester of (meth) acrylic acid such as methyl (meth)acrylate, ethyl (meth) acyate, butyl (meth)acrylate, 2-ethylhexyl (meth)acrylate, etc.

Furthermore, the cured material characteristics can be improved by using thermoplastic organic polymers along with polymerizable compounds having the above ethylenically unsaturat d bonds. Examples of these thermoplastic organic polymers include copolymers of (meth)acrylic acid ester compounds and (meth)acrylic acid, copolymers of (meth)acrylic acid ester compounds, (meth)acrylic acids, and other vinyl monomers capable of being copolymerized thereof, etc.

The above (meth)acrylic acid ester compounds include methyl(meth)acrylate, ethyl (meth)acrylate, butyl (meth) acrylate, 2-ethylhexyl (meth)acrylate, tetrahydrofurfyl (meth)acrylate, t-butyl (meth)acrylate, glycidyl (meth) acrylate, 2,2,2-trifluoroethyl(meth)acrylate, 2,2,3,3-tetrafluoropropyl (meth)acrylate, benzyl (meth)acrylate, etc. Furthermore, the above vinyl monomers include styrene, vinyl toluene, etc.

Synergistic effects can be obtained in the case of combining a compound of the present invention and other existing photopolymerization initiators, and examples of existing photopolymerization initiators that can be used in combination with a compound of the present invention include benzophenone, phenylbiphenylketone, 1-hydroxy-1-benzoylcydohexane, benzyl, benzyldimethylketal, 2-benzyl-2-(dimethylamino)-4'-morpholinobutyrophenone, 2-methyl-4'-(methylthio)-2-morpholinopropiophenone, thioxanthone, 1-chloro-4-propyloxythloxanthone, isopropylthioxanthone, diethylthioxanthone, ethylanthraquinone, 4-benzoyl-4'-methyldiphenylsulfide, benzoinbutylether, 2-hydroxy-2-methylpropiophenone, 2-hydroxy-2-ethyl 4'-isopropylpropiophenone, 4-butylbenzoyltrichloromethane, 4-phenoxybenzoyl-dichlommethane, methyl benzoylformic acid, 9-phenylacridine, 1,7-bis(9'-acridinyl)heptane, 9-butyl-3,6-bis(2'-morpholinoisobutyloyl)carbazole, 2-methyl-4,6-bis(trichloromethyl)-s-triazine, 2-phenyl 4,6-bis(trichloromethyl)-s-triazine, 2-naphthyl-4,6-bis(trichloromethyl)-s-triazine, 2,4,6-trimethylbenzoyldiphenylphosphine, etc.

Heat polymerization inhibitors such as 4-methoxyphenol, hydroquinone, pyrocatechol, t-buty catechol, phenothiazine, etc., and plasticizers, adhesion promoters, and general additives such as fillers, etc. can be used in a photosensitive composition comprising a compound of the present invention if necessary.

A photosensitive composition comprising a compound of the present invention is used as a solution phased composition to which solvents are added to dissolve or disperse each ingredient mentioned above if necessary.

Examples of the above solvents include acetone, methylethylketone, methylisobutylketone, methylcellosolve, ethylcellosolve, tetrahydrofuran, 1,4-dioxane, ethylene glycol dimethyl ether, ethylene glycol diethyl ether, propylene glycol dimethyl ether, propylene glycol diethyl ether, chloroform, methylene chloride, 1,2-dichloroethane, 1,1,1-trichloroethane, 1,1,2-trichloroethane, 1,1,2-trichloroethene, hexane, heptane, octane, cyclohexane, benzene, toluene, xylene, methanol, ethanol, isopropanol, propanol, butanol, t-butanol, cyclohexanone, propylene glycol methylethercetate, ethyl-3-ethoxypropionate, ethyl cellosolveacetate, methyl cellosolveacetate, butyl acetate, etc.

A photosensitive composition comprising a compound of the present invention is applied on supporting materials such as metal, paper, glass, etc. by methods such as using a roll coater, curtain coater, spin coater, varieties of printings, dipping, etc., and can be transferred to other supporting materials such as film, etc. after coating on the supporting materials. That is, there are no limits in the application methods.

A photosensitive composition comprising a compound of the present invention can be used with photourable paints, photo-curable inks, photo-curable adhesives, printing plates, photoresists for printing circuit boards, pigment dispersion type photoresists for manufacturing TFT LCD (thin film transistor liquid crystal display) color filters, black matrixes, the manufacturing of PDPs (plasma display panels), etc., and there are no particular limits in its applications.

Light sources of which wavelengths emit light of 250 to 450 nm can be used for curing a photosensitive composition comprising compounds of the present invention, and examples include mercury vapor arc, carbon arc, xenon (Xe) arc, etc.

The present invention is again described in detail by the following specific EXAMPLES. However, the following EXAMPLES are only for exemplifying the present invention, which is not limited by the following EXAMPLES.

EXAMPLES

Example 1

Preparation of 3-{4-[2,4-bis(trichloromethyl)-s-triazine-6-yl]phenyl thio}propionic Acid Represented as in the Following Chemical Formula 1a

[Chemical Formula 1a]

[1st Step: Synthesis of 3-(4-cyanophenyl thio)propionic acid]

20 g of 4-fluorobenzonitrile (165 mmol), 20 g of 3-mercaptopropionic acid (188 mmol), and 50 g of potassium carbonate were put into 300 mL of DMF (dimethyl formamide) and reacted for 20 hours by maintaining the bath temperature at 100° C.

After lowering the reaction temperature to room temperature, the reacted solution was slowly poured into 1500 mL of distilled water and the resulting precipitate was filtered off. The filtrate was acidified (pH up to 2 was confirmed by pH paper) with a 2 N HCl solution, thus producing organic material sediment After filtering and washing the sediment with distilled water, the product was dried in a vacuum oven, and the structure was analyzed by the NMR (nuclear magnetic resonance) method. The yield was ov r 86%.

[2nd Step: Synthesis of 3-{4-[2,4-bis(trichloromethyl)-s-triazine-6-yl]phenyl thio}propionic acid]

The reaction mixture of 22 g of 3-(4-cyanophenyl thio)propionic acid, 150 g of trichloroacetonitrile, and 2 g of AlBr$_3$ was heated to 60° C. in order to dissolve the initially undissolved starting materials, and was bubbled by dry HCl at room temperature.

The product was slowly formed as time passed. After stopping the reaction after 24 hours, the product was extracted with 1000 mL of diethyl ether, washed with ion exchange water (DI water), and dried over anhydrous magnesium sulfate.

All volatile materials were removed under vacuum, and crystallization was induced with methanol and water obtaining a compound having over an 67% yield. The structure of this compound was analyzed by NMR, FT-IR, and UV-vis. spectrophotometer as represented in the following Table 1.

TABLE 1

| | |
|---|---|
| $^1$H NMR (CDCl$_3$, ppm) | 9.03(1H, broad peak, COOH), 8.57(2H, d, Ar—H), 7.41(2H, d, Ar—H), 3.30(2H, t, —CH$_2$—S), 2.78(2H, t, —CH$_2$—) |
| UV-vis, (nm) | $\lambda_{max}$ = 356 |

Example 2

Preparation of 1,1,1,3,3,3-hexafluoroisopropyl-3-{4-[2,4-bis(trichloromethyl)-s-triazine-6-yl]phenyl thio}propionate Represented as in the Following Chemical Formula 1b

[Chemical Formula 1b]

[1st Step: Synthesis of 3-(4-cyanophenyl thio)propionic acid]

20 g of 4-fluorobenzonitrile (165 mmol), 20 g of 3-mercaptopropionic acid (188 mmol), and 50 g of potassium carbonate w re put into 300 mL of DMF (dimethyl formamide) and reacted for 20 hours by maintaining be bath temperature at 100° C.

After lowering the reaction temperature to room temperature, the reacted solution was slowly poured into 1500 mL of distilled water and the resulting precipitate was filtered off. The filtrate was acidified (pH up to 2 was confirmed by pH paper) with a 2 N HCl solution, thus producing organic material sediment. After filtering and washing the sediment with distilled water, the product was dried in a vacuum oven, and the structure was analyzed by the NMR (nuclear magnetic resonance) method. The yield was over 86%.

[2nd Step: Synthesis of 1,1,1,3,3,3-hexafluoroisopropyl-3-(4-cyanophenyl thio)propionate]

After mixing 8 g of 3-(4-cyanophenyl thio)propionic acid (38.6 mmol) and 30 g of thionyl chloride at room temperature, the mixture was reacted at a temperature of 60° C. for 5 hours. In this process, thionyl chloride was is used as a reagent and solvent.

After removing unreacted thionyl chloride, the resulting acid chloride was dissolved in 50 mL of THF (tetrahydrofuran). 5 g of pyridine and 10 g of hexafluoroisopropyl alcohol was slowly added to the reactor, and then the reaction mixture was reacted by stirring at room temperature for 15 hours.

After the reaction, salts were removed with 500 mL of distilled water and the product was extracted by ethyl ether.

The compound was separated by the column chromatography method with hexane and ethyl ether mixed solvent(1:1 of volume ratio) as an eluent. The yield was around 40%.

[3rd Step: Synthesis of 1,1,1,3,3,3-hexafluoroisopropyl-3-{4-[2,4-bis(trichloromethyl)-s-triazine-6-yl]phenyl thio}propionate]

3.5 g of 1,1,1,3,3,3-hexafluoroisopropyl-3-(4-cyanophenylthio)propionate (10 mmol), 0.5 g of AlBr$_3$, and 30 g of trichloroacetonitrile solution were bubbled by dry HCl at room temperature.

The product was slowly formed as time passed, and was solidified after 24 hours.

After finishing the reaction, the resultant was extracted with 1000 mL of diethyl ether, washed with ion exchange water (DI water), and dried over anhydrous magnesium sulfate. All volatile materials were removed under vacuum and the product was recrystallized from methanol to give yellow crystal in 83% yield. The structure of the product was analyzed by NMR, FT-IR, and UV-vis. spectrophotometer as represented in the following Table 2.

TABLE 2

| $^1$H NMR (CDCl$_3$, ppm) | 8.62(2H, d, Ar—H), 7,45(2H, d, Ar—H), 5.77(1H, m, OCH), 3.38(2H, t, —CH$_2$—S), 2.93(2H, t, —CH$_2$—) |
|---|---|
| UV-vis, (nm) | $\lambda_{max}$ = 354 |

Example 3

Preparation of Ethyl 2-{4-[2,4-bis(trichloromethyl)-s-triazine-6-yl]phenyl thio}acetate Represented as in the Following Chemical Formula 1c

[Chemical Formula 1c]

[1st Step: Synthesis of Ethyl 2-(4-cyanophenyl thio)acetate]

15 g of 4-fluorobenzonitrile (124 mmol), 16 g of ethyl 2-mercaptoacetate (133 mmol), and 25 g of potassium carbonate were put into 100 mL of DMF (dimethyl formamide) and reacted for 20 hours by maintaining the bath temperature at 130° C.

After lowering the reaction temperature to room temperature, the reacted solution was slowly poured into 700 mL of distilled water, extracted with ethyl ether, washed with distilled water, dried over anhydrous magnesium sulfate, and filtered. And then, volatile materials were evaporated to give a crude product. The product was purified by column chromatography with the mixed solvent of hexane and ethyl acetate (3:1 of volume ratio) as an eluent. The structure of the product was analyzed by the NMR (nuclear magnetic resonance) method. The yield was over 76%.

[2nd Step: Synthesis of Ethyl 2-{4-[2,4-bis(trichloromethyl)-s-triazine-6-yl]phenyl thio}acetate]

The mixed solution of 10 g of ethyl 2-(4-cyanophenyl thio)acetate (45.2 mmol), 0.8 g of AlBr$_3$, and 50 g of trichloroacetonitrile were bubbled with dry HCl at room temperature.

The product was slowly formed with sediments occurring as time passed. After stopping the reaction after 24 hours, the product was extracted with 500 mL of chloroform, washed with ion exchange water (DI water), and dried over anhydrous magnesium sulfate.

After removing all volatile materials under vacuum, the compound was separated by column chromatography with the mixed solvent of hexane and ethyl acetate (3:1 of volume ratio) as an eluent in over 82% yield. The structure of this compound was analyzed by NMR, FT-IR, and UV-vis. spectrophotometer as represented in the following Table 3.

TABLE 3

| $^1$H NMR (CDCl$_3$, ppm) | 8.58(2H, d, Ar—H), 7.44(2H, d, Ar—H), 4.22(2H, q, O—CH$_2$—), 3.77(2H, s, —CH$_2$—S), 1.25(3H, t, —CH$_3$) |
|---|---|
| UV-vis, (nm) | $\lambda_{max}$ = 352 |

Example 4

Preparation of 2-ethoxyethyl 2-{4-[2,4-bis(trichloromethyl)-s-triazine-6-yl]phenyl thio}acetate Represented as in the Following Chemical Formula 1d

[Chemical Formula 1d]

The mixed solution of 10 g of 2-ethoxyethyl 2-(4-cyanophenylthio)acetate (37.7 mmol), 0.8 g of AlBr$_3$, and 50 g of trichloroacetonitrile was bubbled with dry HCl at room temperature.

The product was slowly formed with sediments occurring as time passed. After stopping the reaction after 24 hours, the product was extracted with 500 ml of chloroform, washed with ion exchange water (DI water), and dried over anhydrous magnesium sulfate.

After removing all volatile materials under vacuum, the compound was separated by column chromatography with the mixed solvent of hexane and ethyl acetate (3:1 of volume ratio) as an eluent in an 86% yield. The structure of this compound was analyzed by NMR, FT-IR, and UV-vis. spectrophotometer as represented in the following Table 4.

TABLE 4

| $^1$H NMR (CDCl$_3$, ppm) | 8.57(2H, d, Ar—H), 7.42(2H, d, Ar—H), 4.17(2H, t, —CO$_2$—CH$_2$—), 3.75(2H, s, —CH$_2$—S), 1.22(3H, t, —CH$_3$) |
|---|---|
| UV-vis, (nm) | $\lambda_{max}$ = 353 |

Example 5

Preparation of Cyclohexyl 2-{4-[2,4-bis(trichloromethyl)-s-triazine-6-yl]phenyl thio}acetate Represented as in the Following Chemical Formula 1e

[Chemical Formula 1e]

The mixed solution of 10 g of cyclohexyl 2-(4-cyanophenylthio)acetate (36.3 mmol), 0.8 g of AlBr$_3$, and 50 g of trichloroacetonitrile was bubbled with dry HCl at room temperature.

The product was slowly formed with sediments occurring as time passed. After stopping the reaction after 24 hours, the product was extracted with 500 mL of chloroform, washed with ion exchange water (DI water), and dried over anhydrous magnesium sulfate.

After removing all volatile materials under vacuum, the compound was separated by column chromatography with the mixed solvent of hexane and ethyl acetate (3:1 of volume ratio) as an eluent in an 89% yield. The structure of this compound was analyzed by NMR, FT-IR, and UV-vis. spectrophotometer as represented in the following Table 5.

TABLE 5

| $^1$H NMR(CDCl$_3$, ppm) | 8.57(2H, d, Ar—H), 7.42(2H, d, Ar—H), 4.77(1H, m, —CO$_2$—CH—), 3.76(2H, s, —CH$_2$—S) |
|---|---|
| UV-vis, (nm) | $\lambda_{max}$ = 354 |

Example 6

Preparation of Benzyl 2-{4-[2,4-bis (trichloromethyl)-s-triazine-6-yl]phenyl thio}acetate Represented as in the Following Chemical Formula 1f

[Chemical Formula 1f]

The mixed solution of 10 g of benzyl 2-(4-cyanophenylthio)acetate (35.3 mmol), 0.8 g of AlBr$_3$, and 50 g of trichloroacetonitrile was bubbled by dry HCl at room temperature.

The product was slowly formed with sediments occurring as time passed. After stopping the reaction after 24 hours, the product was extracted with 500 mL of chloroform, washed with ion exchange water (DI water), and dried over anhydrous magnesium sulfate.

After removing all volatile materials under vacuum, the compound was separated by column chromatography with the mixed solvent of hexane and ethyl acetate (3:1 of volume ratio) as an eluent in a 91% yield. The structure of this compound was analyzed by NMR, FT-IR, and UV-vis. spectrophotometer as represented in the following Table 6.

TABLE 6

| $^1$H NMR(CDCl$_3$, ppm) | 8.57(2H, d, Ar—H), 7.42(2H, d, Ar—H), 7.33(5H, m, Ar—H), 4.99(2H, s, —CO$_2$—CH$_2$—), 3.75(2H, s, —CH$_2$—S) |
|---|---|
| UV-vis (nm) | $\lambda_{max}$ = 352 |

Example 7

Preparation of 3-{3-chloro-4-[2,4-bis (trichloromethyl)-s-triazine-6-yl]phenyl thio}propionic Acid Represented as in the Following Chemical Formula 1g

[Chemical Formula 1g]

[1st Step: Synthesis of 3-[(3-chloro-4-cyanophenyl) thio] propionic acid]

5 g of 3-chloro-4-fluorobenzonitrile (32.1 mmol), 3.58 g of 3-mercaptopropionic acid (33.7 mmol), and 11.1 g of potassium carbonate (80.4 mmol) were put into 50 mL of DMF (dimethyl formamide) and reacted for 15 hours by maintaining the bath temperature at 100° C.

After lowering the reaction temperature to room temperature, the reacted solution was slowly poured into 1500 mL of distilled water and th resulting precipitate was filtered off. The filtrate was acidified (pH up to 4 was confirmed by pH paper) with a 4 N HCl solution, thus producing organic material sediment. After filtering and washing the sediment with distilled water, the product was dried in a vacuum oven, and the structure was analyzed by the NMR (nuclear magnetic resonance) method. The yield was over 80%.

[2nd Step: Synthesis of 3-{3-chloro-4-[2,4-bis (trichloromethyl)-s-triazine-6-yl]phenyl thio}propionic acid]

After putting 5 g of 3-[(3-chloro-4-cyanophenyl) thio] propionic acid (20.7 mmol) and 50 g of trichloroacetonitrile (346.3 mmol) into a reactor, the solution was heated to 60° C. to dissolve the starting materials. After adding 0.5 g of AlBr$_3$ to the mixed solution, the resulting reaction mixture was bubbled with dry HCl.

The product was slowly formed as time passed. After stopping the reaction 24 hours after the formation, the product was extracted with 200 mL of methylene chloride, washed with ion exchange water (DI water), and dried over anhydrous magnesium sulfate.

After carrying out the first crystallization by adding hexane to the resulting methylene chloride solution, the second recrystallization was induced from methanol by adding water at 0° C. The structure of this compound was analyzed by NMR and UV-vis. spectrophotometer as represented in the following Table 7.

TABLE 7

| $^1$H NMR (acetone-d$_6$, ppm) | ~10(1H, broad peak, COOH), 8.55(1H, d, Ar—H), 8.54(1H, s, Ar—H), 7.66(1H, d, Ar—H), 3.40(2H, t, —CH$_2$—S), 2.82(2H, t, —CH$_2$—) |
|---|---|
| UV-vis (nm) | $\lambda_{max}$ = 357 |

Example 8

Preparation of 3-{4-[2,4-bis(trichloromethyl)-s-triazine-6-yl]phenyl thio}propionamide Represented as in the Following Chemical Formula 1h

[Chemical Formula 1h]

The compound represented in Chemical Formula 1h was formed as a byproduct of the preparation of the compound represented in Chemical Formula 1, and easily separated through column chromatography using ethyl acetate as an eluent The structure of this compound was analyzed by NMR, and UV-vis. spectrophotometer as represented in the following Table 8.

TABLE 8

| | |
|---|---|
| $^1$H NMR (acetone-d$_6$, ppm) | 8.54(2H, d, Ar—H), 7.54(2H, d, Ar—H), 6.99(1H, s, N—H), 6.51(1H, s, N—H), 3.36(2H, t, —CH$_2$—S), 2.78(2H, t, —CH$_2$—) |
| UV-vis (nm) | $\lambda_{max}$ = 356 |

Example 9

Constituents comprising a compound of Chemical Formula 1a of EXAMPLE 1 as represented in the following Table 9 and zircomia beads of 0.3 mmϕ were put into a bead mill, mixed, and dispersed for 20 hours for the preparation of a photosensitive composition, and the stable dispersion condition was maintained after storing the solution in an ultraviolet ray-shielded room at room temperature about 10 days after milling and filtering with 4.5 micron filters.

TABLE 9

| Classification | Names of raw materials | Content (weight parts) |
|---|---|---|
| Pigment | C.I. pigment red 177 | 90 |
| Binder | BzMA:MAA:HEMA = 65:25:10 Mw: 40,000 | 50 |
| Polymerizable compound | Dipentaerythritol hexaacrylate | 40 |
| Photopolymerization initiator | 3-{4-[2,4-bis(trichloromethyl)-s-triazine-6-yl]phenyl thio} propionic acid | 30 |
| Organic solvent | PGMEA (boiling point: 146° C.) | 790 |

An uniform film with a thickness of about 2 μm was formed by spin-coating this photosensitive composition solution on glass and prebaking at a temperature from 80 to 90° C. for two minutes.

This sample was exposed to light through a photomask under a high pressure mercury lamp at an energy of 200 mJ/cm$^2$ to form an image.

The light-exposed sample was developed at a temperature of 25° C. for various times with an aqueous KOH solution of pH 11.4 to give a resist pattern, washed with deionized water, and postbaked at 200° C. for about 60 minutes. It was confirmed that dean patterns were formed without resist residues as a result of observing film conditions on the glass surface with an optical microscope.

Example 10

After preparing a photosensitive composition comprising constituents including a compound of Chemical Formula 1a of EXAMPLE 1 as represented in the following Table 10 in the same method as in EXAMPLE 1, it could be known that clean patterns were formed as a result of observing film conditions on the glass surface with an optical microscope.

TABLE 10

| Classification | Names of raw materials | Content (weight parts) |
|---|---|---|
| Pigment | C.I. pigment red 177 | 90 |
| Binder | BzMA:MAA = 75:25 Mw: 35,000 | 50 |
| Polymerizable compound | Dipentaerythritol hexaacrylate | 40 |
| Photopolymerization initiator | 3-{4-[2,4-bis(trichloromethyl)-s-triazine-6-yl]phenyl thio} propionic acid | 30 |
| Organic solvent | PGMEA (boiling point: 146° C.) | 790 |

Example 11

After preparing a photosensitive composition comprising constituents including a compound of Chemical Formula 1b of EXAMPLE 2 as represented in the following Table 11 in the same method as in EXAMPLE 1, it could be known that clean patterns were formed as a result of observing film conditions on the glass surface with an optical microscope.

TABLE 11

| Classification | Names of raw materials | Content (weight parts) |
|---|---|---|
| Pigment | C.I. pigment red 177 | 90 |
| Binder | BzMA:MAA:HEMA = 85:25:10 Mw: 40,000 | 50 |
| Polymerizable compound | Dipentaerythritol hexaacrylate | 40 |
| Photopolymerization initiator | 1,1,1,3,3,3-hexafluoroisopropyl-3-{4-[2,4-bis(trichloromethyl)-s-triazine-6-yl]phenyl)thio} propionate | 30 |
| Organic solvent | PGMEA (boiling point: 146° C.) | 790 |

Example 12

After preparing a photosensitive composition comprising constituents including a compound of Chemical Formula 1a of EXAMPLE 1 as represented in the following Table 12 in the same method as in EXAMPLE 1, it could be known that clean patterns were formed as a result of observing film conditions on the glass surface with an optical microscope.

TABLE 12

| Classification | Names of raw materials | Content (weight parts) |
|---|---|---|
| Pigment | C.I. pigment red 177 | 90 |
| Binder | BzMA:MAA:HEMA = 65:25:10 Mw: 40,000 | 50 |

TABLE 12-continued

| Classification | Names of raw materials | Content (weight parts) |
|---|---|---|
| Polymerizable compound | Dipentaerythritol hexaacrylate | 40 |
| Photopolymerization initiator | 3-{4-[2,4-bis(trichloromethyl)-s-triazine-6-yl]phenyl thio} propionic acid | 15 |
| | (±)2-benzyl-2-(dimethylamino-4'-morpholinobutyrophenone (Aldrich) | 15 |
| Organic solvent | PGMEA (boiling point: 146° C.) | 790 |

Example 13

After preparing a photosensitive composition comprising constituents including a compound of Chemical Formula 1b of EXAMPLE 2 as represented in the following Table 13 in the same method as in EXAMPLE 1, it could be known that clean patterns were formed as a result of observing film conditions on the glass surface with an optical microscope.

TABLE 13

| Classification | Names of raw materials | Content (weight parts) |
|---|---|---|
| Pigment | C.I. pigment red 177 | 90 |
| Binder | BzMA:MAA:HEMA = 65:25:10 Mw: 40,000 | 50 |
| Polymerizable compound | Dipentaerythritol hexaacrylate | 40 |
| Photopolymerization initiator | 1,1,1,3,3,3-hexafluoroisopropyl-3-{4-[2,4-bis(trichloromethyl)-s-triazine-6-yl]phenyl thio} propionate | 15 |
| | (±)2-benzyl-2-(dimethylamino-4'-morpholinobutyrophenone (Aldrich) | 15 |
| Organic solvent | PGMEA (boiling point: 146° C.) | 790 |

Comparative Example 1

Several photosensitive compositions comprising constituents of EXAMPLE 9 but using different photopolymerization initiators were prepared under the same conditions as in EXAMPLE 9 in order to investigate the effect of photoinitiators on process characteristics, particularly development time.

Compounds represented respectively in Chemical Formula 1a, 1b, 1c, 1g, and 1h and 2,4-bis(trichloromethyl)-(4'-methoxystyryl)-6-s-trazine (TAZ 110) represented in the following Chemical Formula 1i were comparatively used.

[Chemical Formula 1i]

The development time is represented as in the following Table 14 when patterns were developed with an aqueous KOH solution of pH 11.4. The development time can be radically reduced and there were no resist residues on the glass surfaces after the development in the case of using photopolymerization initiators(formula 1a, formula 1g) having carboxylic acid groups.

TABLE 14

| Classification | Compound of Chemical Formula 1a | Compound of Chemical Formula 1b | Compound of Chemical Formula 1c | Compound of Chemical Formula 1g | Compound of Chemical Formula 1h | Compound of Chemical Formula 1i |
|---|---|---|---|---|---|---|
| Development time (sec) | 30 | 62 | 60 | 35 | 55 | 65 |

A triazine-based photoinitiator having functionalized alkylthio groups of the present invention not only shows strong absorbance at 360 nm, but it is also superior in long term storage stability at room temperature, in photochemical activity, in development time control, and in coating characteristics when being employed in a photosensitive composition.

While the present invention has been described in detail with reference to the preferred embodiments, those skilled in the art will appreciate that various modifications and substitutions can be made thereto without departing from the spirit and scope of the present invention as set forth in the appended claims.

What is claimed is:

1. A triazine compound comprising a functionalized alkylthio group represented in the following Chemical Formula 1:

[Chemical Formula 1]

wherein $R_1$ is selected from the group consisting of $C_nH_{2n}CONH_2$ (n is an integer from 1 to 12), $C_nH_{2n}COOC_mH_{2m+1}$ (n is an integer from 1 to 12 and m is an integer from 0 to 12), $(CH_2)_nCOOC_mH_{2m}OC_lH_{2l+1}$ (n, m, and l are each independent integers from 1 to 12), $(CH_2)_nCOO$-cyclo-$C_mH_{2m+1}$ (n is an integer from 1 to 12, and m is an integer from 3 to 12), $C_nH_{2n}COOR_f$ (n is an integer from 1 to 12, and $R_f$ is an alkyl group of which all or some of the hydrogen atoms are substituted with fluorine), and $C_nH_{2n}COOR_6$ (n is an integer from 1 to 12, and $R_6$ is an aryl group having from 6 to 14 carbon atoms or a $C_1$~$C_6$ alkyl group having a $C_6$~$C_{14}$ aryl group); and $R_2$, $R_3$, $R_4$, and $R_5$ are each independent hydrogens, halogens, or alkyls having from 1 to 6 carbon atoms, or alkoxyl groups having from 1 to 6 carbon atoms.

2. A compound represented in the following Chemical Formula 1a in accordance with claim 1:

[Chemical Formula 1a]

3. A compound represented in the following Chemical Formula 1b in accordance with claim 1:

[Chemical Formula 1b]

4. A compound represented in the following Chemical Formula 1c in accordance with claim 1:

[Chemical Formula 1c]

5. A compound represented in the following Chemical Formula 1d in accordance with claim 1:

[Chemical Formula 1d]

6. A compound represented in the following Chemical Formula 1e in accordance with claim 1:

[Chemical Formula 1e]

7. A compound represented in the following Chemical Formula 1f in accordance with claim 1:

[Chemical Formula 1f]

8. A compound represented in the following Chemical Formula 1g in accordance with claim 1:

[Chemical Formula 1g]

9. A compound represented in the following Chemical Formula 1h in accordance with claim 1:

[Chemical Formula 1h]

10. A method for preparing a triazine compound comprising a functionalized alkylthio group represented in the following Chemical Formula 1:

[Chemical Formula 1]

wherein $R_1$ is selected from the group consisting of $C_nH_{2n}CONH_2$ (n is an integer from 1 to 12), $C_nH_{2n}COOC_mH_{2m+1}$ (n is an integer from 1 to 12 and m is an integer from 0 to 12), $(CH_2)_n COOC_mH_{2m}OC_lH_{2l+1}$ (n, m, and l are each independent integers from 1 to 12), $(CH_2)_nCOO\text{-cyclo-}C_mH_{2m+1}$ (n is an integer from 1 to 12, and m is an integer from 3 to 12), $C_nH_{2n}COOR_f$ (n is an integer from 1 to 12, and $R_f$ is an alkyl group of which all or some of the hydrogen atoms are substituted with fluorine), and $C_nH_{2n}COOR_6$ (n is an integer from 1 to 12, and $R_6$ is an aryl group having from 6 to 14 carbon atoms or a $C_1$~$C_6$ alkyl group having a $C_6$~$C_{14}$ aryl group); and $R_2$, $R_3$, $R_4$, and $R_5$ are each independent hydrogens, halogens, or alkyls having from 1 to 6 carbon atoms, or alkoxyl group having from 1 to 6 carbon atoms;

wherein the preparation method comprises the step of reacting an alkylthiobenzonitrile compound comprising a functional group represented as in the following Chemical Formula 2 with trichloroacetonitrile (CCl$_3$CN) under the existence of aluminum halide (AlC$_3$, AlBr$_3$):

[Chemical Formula 2]

wherein R$_1$ is selected from the group consisting of C$_n$H$_{2n}$CONH$_2$ (n is an integer from 1 to 12), C$_n$H$_{2n}$COOC$_m$H$_{2m+1}$ (n is an integer from 1 to 12 and m is an integer from 0 to 12), (CH$_2$)$_n$COOC$_m$H$_{2m}$OC$_l$H$_{2l+1}$ (n, m, and l are each independent integers from 1 to 12), (CH$_2$)$_n$COO-cyclo-C$_m$H$_{2m-1}$ (n is an integer from 1 to 12, and m is an integer from 3 to 12), C$_n$H$_{2n}$COOR$_f$ (n is an integer from 1 to 12, and R$_f$ is an alkyl group of which all or some of the hydrogen atoms are substituted with fluorine), and C$_n$H$_{2n}$COOR$_6$ (n is an integer from 1 to 12, and R$_6$ is an aryl group having from 6 to 14 carbon atoms or a C$_1$~C$_6$ alkyl group having a C$_6$~C$_{14}$ aryl group); and R$_2$, R$_3$, R$_4$, and R$_5$ are each independent hydrogens, halogens, or alkyls having from 1 to 6 carbon atoms, or alkoxyl groups having from 1 to 6 carbon atoms.

11. A combined polymerization initiator comprising: a photoinitiator selected from the group consisting of benzophenone, phenylbiphenylketone, 1-hydroxy-1 benzoylcyclohexane, benzyl, benzyldimethylketal, 2-benzyl-2-dimethylamino)-4'-morpholinobutyrophenone, 2-methyl-4'-methylthio)-2-morpholinopropiophenone, thioxanthone, 1-chloro-4-propyloxythioxanthone, isopropylthioxanthone, diethylthioxanthone, ethylanthraquinone, 4-benzoyl-4'-methyldiphenylsulfide, benzoinbutylether, 2-hydroxy-2-methylpropiophenone, 2-hydroxy-2-methyl-4'-isopropylpropiophenone, 4-butylbenzoyltrichloromethane, 4-phenoxybenzoyldichloromethane, methyl benzoylformic acid, 9-phenylacridine, 1,7-bis(9'-acridinyl)heptane, 9-n-but-3,6-bis(2'-morpholinoisobutyloyl)carbazole, 2-methyl-4,6-bis(trichloromethyl)-s-triazine, 2-phenyl-4,6-bis(trichloromethyl)-s-triazine, 2-naphthyl-4,6-bis(trichloromethyl)-s-triazine, 2,4,6-methylbenzoyldiphenylphosphine; and a triazine derivative represented in the following Chemical Formula 1 as an active ingredient:

[Chemical Formula 1]

wherein R$_1$ is selected from the group consisting of C$_n$H$_{2n}$CONH$_2$ (n is an integer from 1 to 12), C$_n$H$_{2n}$COOC$_m$H$_{2m+1}$ (n is an integer from 1 to 12 and m is an integer from 0 to 12), (CH$_2$)$_n$COOC$_m$H$_{2m}$OC$_l$H$_{2l+1}$ (n, m, and l are each independent integers from 1 to 12), (CH$_2$)$_n$COO-cyclo-C$_m$H$_{2m+1}$ (n is an integer from 1 to 12, and m is an integer from 3 to 12), C$_n$H$_{2n}$COOR$_f$ (n is an integer from 1 to 12, and R$_f$ is an alkyl group of which all or some of the hydrogen atoms are substituted with fluorine), and C$_n$H$_{2n}$COOR$_6$ (n is an integer from 1 to 12, and R$_6$ is an aryl group having from 6 to 14 carbon atoms or a C$_1$~C$_6$ alkyl group having a C$_6$~C$_{14}$ aryl group); and R$_2$, R$_3$, R$_4$, and R$_5$ are each independent hydrogens, halogens, or alkyls having from 1 to 6 carbon atoms, or alkoxyl groups having from 1 to 6 carbon atoms.

12. A photosensitive composition for photo-curable paints, photo-curable inks, photo-curable adhesives, printing plates, photoresists for printing circuit boards, pigment dispersion type photoresists for manufacturing TFT LCD color filters, resin-based photoresists for black matrixes, photopolymerization compositions for plasma display panels or photoresist compositions for manufacturing semiconductors comprising a triazine compound comprising functionalized alkylthio groups represented in the following Chemical Formula 1:

[Chemical Formula 1]

wherein R$_1$ is selected from the group consisting of C$_n$H$_{2n}$CONH$_2$ (n is an integer from 1 to 12), C$_n$H$_{2n}$COOC$_m$H$_{2m+1}$ (n is an integer from 1 to 12 and m is an integer from 0 to 12), (CH$_2$)$_n$COOC$_m$H$_{2m}$OC$_l$H$_{2l+1}$ (n, m, and l are each independent integers from 1 to 12), (CH$_2$)$_n$COO-cyclo-C$_m$H$_{2m-1}$ (n is an integer from 1 to 12, and m is an integer of 3 to 12), C$_n$H$_{2n}$COOR$_f$ (n is an integer from 1 to 12, and R$_f$ is an alkyl group of which all or some of the hydrogen atoms are substituted with fluorine), and C$_n$H$_{2n}$COOR$_6$ (n is an integer from 1 to 12, and R$_6$ is an aryl group having from 6 to 14 carbon atoms or a C$_1$~C$_6$ alkyl group having a C$_6$~C$_{14}$ aryl group); and R$_2$, R$_3$, R$_4$, and R$_5$ are each independent hydrogens, halogens, or alkyls having from 1 to 6 carbon atoms, or alkoxyl groups having from 1 to 6 carbon atoms.

* * * * *